(12) United States Patent
Charafeddine et al.

(10) Patent No.: US 11,957,891 B2
(45) Date of Patent: Apr. 16, 2024

(54) PERCUTANEOUS BLOOD PUMP AND INTRODUCER SYSTEM

(71) Applicant: MODEUS INC., Wilmington, DE (US)

(72) Inventors: Farah Charafeddine, Chehim (LB); Bruce Baker, Placerville, CA (US)

(73) Assignee: Bashar Ballout, Bad Homburg (DE)

( * ) Notice: Subject to any disclaimer, the term of this patent is extended or adjusted under 35 U.S.C. 154(b) by 592 days.

(21) Appl. No.: 17/245,169

(22) Filed: Apr. 30, 2021

(65) Prior Publication Data
US 2021/0260361 A1    Aug. 26, 2021

Related U.S. Application Data

(63) Continuation of application No. 17/133,245, filed on Dec. 23, 2020, now abandoned, which is a
(Continued)

(51) Int. Cl.
*A61M 60/221* (2021.01)
*A61M 60/13* (2021.01)
(Continued)

(52) U.S. Cl.
CPC .......... *A61M 60/221* (2021.01); *A61M 60/13* (2021.01); *A61M 60/135* (2021.01);
(Continued)

(58) Field of Classification Search
CPC .. A61M 60/221; A61M 60/804; A61M 60/81; A61M 60/419; A61M 60/414;
(Continued)

(56) References Cited

U.S. PATENT DOCUMENTS 5,300,112 A * 4/1994 Barr ...................... A61M 60/88
623/3.15
8,489,190 B2 * 7/2013 Pfeffer ................ A61M 60/808
15/22.1

(Continued)

*Primary Examiner* — Erin M Piateski
(74) *Attorney, Agent, or Firm* — Ryan Alley IP

(57) ABSTRACT

The present invention relates to a percutaneous blood pump (1) and an introducer system to be placed in the circulatory system of a patient e.g. using the Seldinger technique without the need of surgical access. The percutaneous blood pump (1) comprises a pump housing (11) inside which a radially pumping impeller (12) is arranged for rotation by means of a rotating flexible cable housed inside a protective flexible catheter (15) and attached to a bearing housing (21) in which a set of radial and axial bearings are housed and arranged for rotation by means of a flexible cable housed inside another protective flexible catheter (25) and driven by an electric motor (30) in a motor housing (31). In addition, an introducer system, comprising an expandable introducer is provided, arranged to facilitate easy and safe introduction of the percutaneous blood pump. The introducer system may comprise a hemostatic valve to limit blood loss during insertion and percutaneous blood pump use. More particularly, the present invention relates to a per-cutaneous blood pump that can be large enough to deliver full circulatory support and is easily and safely introduced into the circulatory system by means of an expandable introducer. The introducer system may include a closure device that is configured to close the incision site after removal of the blood pump and introducer.

24 Claims, 12 Drawing Sheets

Related U.S. Application Data continuation of application No. PCT/IB2019/055329, filed on Jun. 25, 2019.

(60) Provisional application No. 62/689,730, filed on Jun. 25, 2018.

(51) Int. Cl.
    *A61M 60/135*     (2021.01)
    *A61M 60/414*     (2021.01)
    *A61M 60/419*     (2021.01)
    *A61M 60/804*     (2021.01)
    *A61M 60/81*     (2021.01)
    *A61M 60/825*     (2021.01)
    *A61M 60/865*     (2021.01)

(52) U.S. Cl.
    CPC ........ *A61M 60/414* (2021.01); *A61M 60/419* (2021.01); *A61M 60/804* (2021.01); *A61M 60/81* (2021.01); *A61M 60/825* (2021.01); *A61M 60/865* (2021.01)

(58) Field of Classification Search
    CPC .. A61M 60/135; A61M 60/13; A61M 60/825; A61M 60/865
    USPC .......................................................... 600/16
    See application file for complete search history.

(56) References Cited

U.S. PATENT DOCUMENTS

2011/0040140 A1*   2/2011   Shifflette ............. A61M 60/216
                                                                 464/62.1
2021/0162109 A1*   6/2021   Neudl .................. A61M 60/38

\* cited by examiner

PERCUTANEOUS BLOOD PUMP AND INTRODUCER SYSTEM

RELATED APPLICATIONS

This application claims priority under 35 U.S.C. § 120 to, and is a continuation of, co-pending application Ser. No. 17/133,245, filed Dec. 23, 2020, which claims priority to International Application PCT/IB2019/055329, filed Jun. 25, 2019 and designating the US, which claims priority to Application 62/689,730, filed Jun. 25, 2018, such application also being claimed priority to under 35 U.S.C. § 119. These US and International applications are incorporated by reference herein in their entireties.

BACKGROUND

Percutaneous blood pumps are well known and are inserted through the peripheral or main circulatory vessels and advanced into the circulatory system to directly or indirectly unload the heart or reduce the heart work load. The dilemma with present percutaneous blood pump is their size and capabilities. A small diameter pump is easy to insert but falls short of delivering full cardiac support while a larger diameter pump is capable of full cardiac support while it is problematic to insert into the circulatory system without the need for a surgical access to expose the insertion vessel. For several decades pump miniaturization was the focus and a 4 mm diameter was the minimal size that was attained. These small pumps required much higher rotational speeds to deliver about 2 liters per minute before the high rotational speed became too damaging to blood. Serious efforts are placed in developing an expandable pump that is inserted in a collapse form and then expanded after insertion. The goal for the expandable device is to create a large diameter pump once inserted in order to attain a high flow rate without increasing the insertion incision size. In parallel, over the past couple decades, catheter technology has managed to decrease catheter diameters used in everyday catheterization to less than 2 mm. So, for today's cardiologists to use a device that requires a 4 mm insertion site became a challenge and presented a high risk to the patient due to the difficulty to close a 4 mm incision site percutaneously and without the need of vessel surgical repair. Therefore, the use of percutaneous blood pumps has been limited to some extent to critical cases and to cardiologists who are well trained in non-standard catheterization.

Additionally, the first generation of percutaneous blood pumps have used a flexible cable to connect the external electric motor to the indwelling blood pump as described in U.S. Pat. No. 4,625,712. The early flexible cables have been plagued by early failure due to the inadequacy of flexible cable designs specifically intended for percutaneous blood pumps requiring high rotational speed and a cyclical loading and unloading due to the loading of these pumps during heart diastole and unloading during heart systole. In addition, the drive cable had to negotiate several curvatures in its path from the external electric motor to the indwelling pump. Another factor that aggravated the endurance of the early drive cable designs is their relatively long length. In other words, the longer the drive cable is the more it is affected by the cyclic loading and unloading. Therefore, a short cable that does not go through any significant curvature will theoretically have a longer life span. The original drive cables were developed from guide wires that were intended to be used as a tracking rail rather than a torque transmission device. In the past two decades drive cable technologies have made significant strides in designing a cable that meet and exceed the requirements of percutaneous blood pumps. In addition, the longer the cable the more debris generated after extended use. Debris were generated due to the friction of the cable metallic elements against each other and in some cases against the flexible protective sheath. This debris must be removed from the system to the outside, so that the patient does not receive a large load of fine metallic debris. Therefore, the shorter the cable the less the winding and unwinding occurs due to loading and unloading of the flexible cable, and the less debris are generated. Therefore, it is plausible that debris generated in a short drive cable would be so minimal that the need to remove this debris to outside the patient's body may not be necessary.

Designs which eliminated the drive cable and integrated the pump housing and electric motor into one long housing eliminated the problem associated with drive cables but added to the difficulties of advancing the pump along the tortuous path into the heart or its advancement inside an introducer sheath. Pushing a long solid cylinder of the combined pump and motor by means of a flexible polymeric catheter inside the closely matched diameter of the introducer sheath in a curved geometry is a challenge. Typically, an introducer sheath with a larger diameter is used to avoid this problem, therefore eliminating some of the advantages offered by the reduced diameter of the device itself. In addition, integrating the electric motor and the pump in a solid housing increased the temperature in the pump area due to the heat generated from the electric motor. Heat in the blood pump is known to be the essential cause in blood clotting and pump failure.

Presently, a significant effort has been placed into expandable blood pumps (U.S. Pat. Nos. 4,919,647; 6,533,716; 7,841,976) that are inserted in a collapsed state and expanded after device insertion. Expandable pumps have been in development for more than a decade and have not yet made it to market due to the technical challenges presented in designing a blood pump that can collapse to a minimal size when inserted and expand to a maximal diameter after insertion and still function repeatedly and consistently without causing damage to the patient or blood. Expanding a stent from a collapsed form to an expanded form is fairly simple, but to expand a rotating impeller from a collapsed form to an expanded diameter and still maintain the aerodynamic foil shape of the impeller blades and maintain close tolerance between the rotating impeller and the surrounding static cannula structure proved to be a greater challenge than initially assumed. The required dimensional accuracy for percutaneous pumps is very high in order to guarantee the safe operation of such devices inside the heart. The rotor and housing of an expandable pump must expand from a collapsed diameter to a precise expanded diameter and immediately start rotating at high speed. Any minor deviation in the dimension of any parts over the course of device operation, which could range up to several weeks, could result in a significant blood damage or device malfunction. Initial clinical trials for the first expandable pump were limited to less than one hour due to the fact that proper pump performance could not be maintained for longer periods.

SUMMARY

The present invention relates to a percutaneous blood pump and an introducer system placed in the circulatory system using the Seldinger technique without the need of surgical access. The percutaneous blood pump comprising a housing inside which a radially pumping impeller is arranged for rotation by means of a rotating flexible cable housed inside a protective flexible catheter and attached to a bearing housing in which a set of radial and axial bearings are housed and arranged for rotation by means of a flexible cable housed inside another protective flexible catheter. In addition, an expandable introducer comprising an expandable frame structure and a polymeric jacket are arranged to facilitate the easy and safe introduction of the above-mentioned percutaneous blood pump and further comprising a hemostatic valve to limit blood loss during insertion and percutaneous blood pump use. More particularly, the present invention relates to a percutaneous blood pump that can be large enough to deliver full circulatory support and is easily and safely introduced into the circulatory system by means of an expandable introducer. Moreover, the present invention relates to a closure device that closes the incision site after device and introducer removal.

It is therefore an object of the present invention to have a percutaneous blood pump with a sufficiently large diameter, preferably ranging from 3 mm to 10 mm, e.g. 4.3 mm, that is inserted with the aid of an expandable introducer set or system that has a minimal diameter, preferably ranging from 1 mm to 7 mm, that allows the easy and safe introduction of a large diameter percutaneous blood pump or any other large diameter device, preferably ranging in diameter from 3 mm to 12 mm. Advantageously, a closure device is part of the introducer set or system that allows vessel closure without the need to surgically repair the vessel.

For clarification, the word "distal" in this application refers to a direction away from the user or a point far away from the user, while "proximal" refers to a direction towards the user or a point that is relatively close to the user, wherein the term "user" refers to a person handling the blood pump, such as a cardiologist, physician or other medical staff. Hence, it is to be understood that the term "distal" refers to directions towards a patient's heart, while the term "proximal" refers to directions away from a patient's heart.

According to an aspect, a percutaneous blood pump is provided, i.e. an intravascular blood pump for percutaneous insertion into a patient's circulatory system, more specifically which may be configured to be introduced into a patient's blood vessel through a puncture or incision site in the patient's skin and further through the patient's circulatory system into the patient's heart. The blood pump comprises a pump housing with an impeller housed in the pump housing, the impeller being rotatable so as to cause blood to be drawn into and through the pump housing, and a motor housing housing an electric motor for causing a rotational movement, the motor housing being distinct from the pump housing and spaced apart from the pump housing in a proximal direction. The blood pump further comprises at least one flexible sheath extending between the motor housing and the pump housing and at least one flexible cable extending through the flexible sheath so as to transfer a rotational movement from the electric motor to the impeller.

By separating the blood pump into at least two distinct housings accommodating different functions of the blood pump, and connecting the distinct housings by way of flexible cables extending through flexible sheaths, the housings can be formed independently and minimized accordingly. This allows providing percutaneous blood pump with a sufficiently large diameter, preferably ranging from 3 mm to 10 mm, e.g. 4.3 mm, in particular with regards to the pump housing the size of which limits the pump performance (liters per minute). Further, the pump has distinct and, thus, shorter stiff sections connected by flexible sections, compared to a percutaneous blood pump formed of a single housing, which houses e.g. both the electric motor and the impeller. Still further, by providing distinct housings for the pump (i.e. the impeller) and the motor, both of which are heat sources of the blood pump, heat generated during operation can be distributed more evenly and will not concentrate on one point in particular, compared to percutaneous blood pumps with a one-piece housing. This allows, for example, the motor to be enlarged, in particular extended in length, if more power is required, without the heat generated exceeding a critical value at any point.

It will be appreciated, while the motor housing is distinct from and spaced apart from the pump housing, the motor housing is likewise inserted into the patient, in contrast to devices with external motors. For instance, while the pump housing may be placed across the aortic valve during operation of the percutaneous blood pump, the motor housing will be located in the ascending aortic, the aortic arch or the descending aorta depending on the length of the at least one flexible sheath and cable between the pump housing and the motor housing. For instance, the flexible sheath, and so the flexible cable, may have a length in the range of about 0.5 mm to about 10 cm, e.g. from about 5 cm to about 10 cm. It will be appreciated that each of the flexible sheaths and cables as mentioned throughout this disclosure may have a length in this range.

The blood pump may further comprise a bearing housing distinct from and arranged between the pump housing and the motor housing, the bearing housing comprising at least one axial and/or radial bearing. A proximal flexible sheath may extend proximally from the bearing housing and a distal flexible sheath may extend distally from the bearing housing, wherein a proximal flexible cable extends through the proximal flexible sheath so as to receive a rotational movement caused by the electric motor and a distal flexible cable extends through the distal flexible sheath so as to transfer the rotational movement to the impeller.

The bearing is particularly configured to take the axial and radial loads introduced by the electric motor. In this way the impeller can be isolated from any excessive axial or radial forces exerted by the electric motor or any other axially exerted force in the system. Therefore, heat generated at the pump head can be reduced, which helps to reduce clotting in the percutaneous blood pump and, therefore, to extend device life as clotting may cause failure of the blood pump.

In an embodiment, the blood pump may further comprising a gear box with a gearing mechanism configured to increase or decrease a speed of a rotational movement transferred from the electric motor to the impeller. The gear box is distinct from the pump housing, the bearing housing and the motor housing and is preferably arranged between the bearing housing and the motor housing although it may be envisioned that the gear box is arranged between the bearing housing and the pump housing. A middle flexible sheath may extend between the gear box and the bearing housing (or the bearing housing and the pump housing), wherein the distal flexible sheath preferably extends distally from the bearing housing. A middle flexible cable may extend through the middle flexible sheath so as to transfer the rotational movement at increased or decreased speed from the gearing mechanism to the bearing.

The pump housing may comprise at least one radial and/or axial bearing configured to center the impeller inside the pump housing. The pump housing may further comprise at least one magnet to form a magnetic coupling between the impeller and the at least one flexible cable.

Preferably, a further proximal flexible sheath is provided extending proximally from the motor housing with at least one electric wire extending through the further proximal flexible sheath and connected to the electric motor to supply electric power to the electric motor. Thus, as mentioned above, while the motor housing is distinct from and spaced apart from the pump housing, the motor housing is likewise inserted into the patient, while the further proximal sheath with the electric wires has a length to extend out of the patient to an external control unit during operation of the blood pump.

In an embodiment, at least one of the flexible cables may comprise a plurality of cable elements that are coupled to each other in series to form the flexible cable. More specifically, the cable elements may be coupled to each other such that a rotational movement can be transferred by means of the flexible cable by applying a torque, wherein the cable elements are at least partially configured to decouple from each other if the applied torque exceeds a predetermined maximum torque. In particular, the cable elements may comprise a plurality of snap elements that are fitted together to form a snap drive cable. Each of the snap elements may have a ball and a cup, the ball configured to snap and rotationally lock inside a cup of another snap element. Further, each of the snap elements may have a locking tip and a locking groove, wherein the locking tip is configured to mechanically engage a locking groove of another snap element, wherein an extent of force of engagement of the locking tip and locking groove determines the maximum torque the snap drive cable can transmit before the locking tip mechanically disengages from the locking groove to thereby decouple the snap elements from each other. Alternatively or in addition, the cable elements may be coupled to each other via magnetic couplings.

Limiting the maximum torque that the snap drive cable can transmit reduces the risk associated with existing drive cables. Solid drive cables can transmit a very high torque and in case of device malfunction the cable will continue to rotate with the potential of perforating its pro-tective sheath and ultimately causing severe damage to surrounding tissue and possibly pa-tient's death. Apart from that, a drive cable made from snap elements allows for greater curvature than existing wire wound drive cable without the risk of failure or wear.

The percutaneous blood pump may further comprise an inflow cannula extending distally from the pump housing, being fluidly coupled to the pump housing and providing a blood flow inlet at a distal end portion. Further, an expandable outflow cannula may be provided, with a distal end of the outflow cannula attached to the pump housing and the outflow cannula extending proximally from the pump housing so as to be placed across a heart valve separating its distal end from its proximal end to create a one way fluid flow through the percutaneous blood pump. The outflow cannula may comprise longitudinal reinforcements, preferably made of a shape-memory material, such as Nitinol, extending from the cannula's proximal end to its distal end, wherein the longitudinal reinforcements attach to a annular ring at the proximal end of the outflow cannula that is placed around the flexible sheath to allow a sliding movement of the annular ring along the flexible sheath.

In an embodiment, a pump head cage may be provided extending distally from the pump housing and configured to keep the pump housing away from surrounding tissue. The pump head cage may be provided as a pump head sensor cage configured to function as a sensor sensing at least one of the position of the individual parts of the cage and thereby a the distance of pump housing from the surrounding tissue, a contraction phase of the ventricle, relative or absolute ventricular volume, a speed of ventricular contraction, an ejection fraction of the ventricle, a location of any localized infracted myocardium, and an electrocardiography (EKG) of the heart.

According to another aspect, an introducer system is provided, which may be particularly configured for introduction of a percutaneous blood pump into a patient's vessel, in particular a percutaneous blood pump as described herein. The introducer system may be provided as an expandable introducer set and comprises an expandable structure, a dilator and an insertion sheath, wherein the insertion sheath has a tubular body that is configured to receive the expandable structure in a compressed form and the dilator inside the expandable structure to form a structure that is configured to be inserted as a unity into the patient's vessel, wherein the expandable structure is configured to be advanced out of the insertion sheath to allow the expandable structure to expand from the compressed form to an expanded form with increased diameter compared to the compressed form.

The introducer system may further comprising a vessel dilating balloon catheter, which is configured to expand the expandable structure by inflating the balloon catheter inside the expandable structure to cause a permanent deformation and expansion of expandable structure. Alternatively or in addition, the expandable structure may be a tubular metallic structure such as nitinol, or polymeric structure that self-expands.

The vessel dilating balloon catheter may comprise a catheter and one or more dilating balloons, the catheter having an inner lumen along its length to allow passage of a guide wire, and at least one of the dilating balloons is in communication with the vessel dilating balloon catheter by means of a separate lumen adjacent to the inner lumen, which allows the passage of fluid to cause balloon inflation or deflation.

The introducer system may further comprise at least one of an inner liner and an outer liner. The inner liner may be configured to line an inner surface of the expandable structure and may be a thin polymeric or non-polymeric jacket ranging in thickness from 0.001 mm to 0.5 mm, wherein the inner liner may be at least partially attached to the inner surface of the expandable structure or free floating. The outer liner may be configured to line an outer surface of the expandable structure and configured to abut an inner wall of the patient's vessel, wherein the outer liner may be at least partially attached to an outer surface of the expandable structure or free floating.

The introducer system may further comprise a dilator balloon catheter and an outer balloon, wherein the dilator balloon catheter may be mounted on an outer surface of the dilator and may be configured to be inflated after the expandable structure is expanded to provide inner support to the expandable structure, wherein the outer balloon is configured to be inflated while the dilator balloon catheter is inflated to provide support to the expandable structure, thereby dilating the target vessel rather than compressing the expandable structure.

The introducer system may further comprise a closure device that is configured for closing a puncture site through which the insertion sheath has been inserted into the patient's vessel after removal of the insertion sheath.

DETAILED DESCRIPTION OF THE PREFERRED EMBODIMENTS

Figure 1:
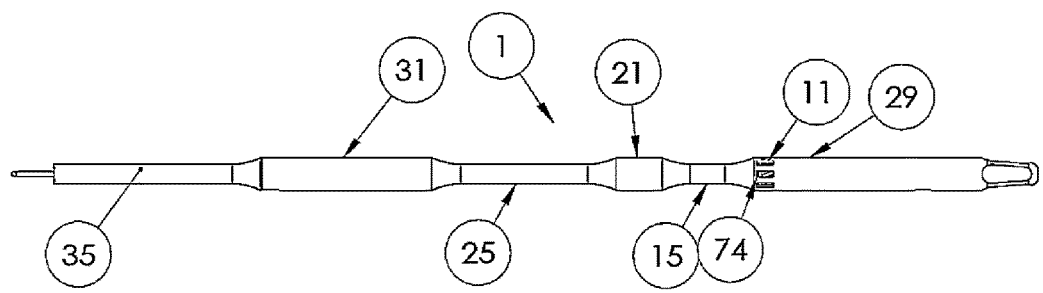
FIG. 1 shows a lateral view of a first embodiment of a segmented blood pump.
Figure 2:
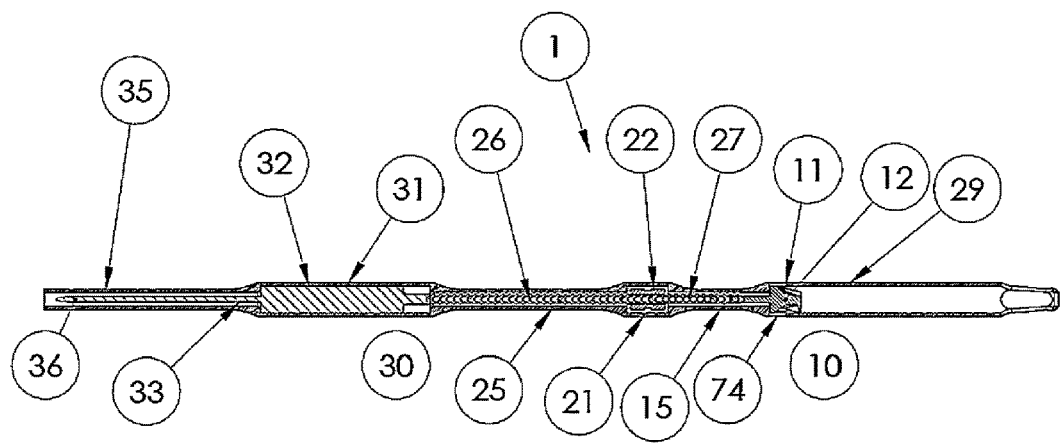
FIG. 2 shows a sectional view of segmented blood pump shown in FIG. 1.

FIGS. 1 and 2 show a percutaneous blood pump 1 according to a first embodiment comprising a pump head 10 connected proximally to a bearing housing 21 by means of a distal catheter sheath 15, wherein the bearing housing 21 is connected proximally to a motor housing 31 by means of a middle catheter sheath 25, wherein the motor housing 30 is connected proximally to a proximal catheter sheath 35 as will be described in more detail below.

As illustrated in the cross-sectional view of FIG. 2, the pump head 10 comprises an impeller 12 that is housed inside a pump housing 11. The impeller 12 is a mixed flow hydraulic rotor intended to move fluid, in particular blood, from its distal to its proximal end upon rotation. The impeller 12 is depicted as a mixed flow hydraulic rotor in this embodiment but could be a centrifugal or an axial hydraulic rotor without affecting the purpose of this invention. The pump housing 11 houses the impeller 12 to keep the impeller 12 from contacting surrounding tissue during operation and is configured to channel pumped fluid from the distal to the proximal end and away from the impeller 12. An inflow cannula 29 is attached to the pump housing 11 and forms or extends to the distal end of the percutaneous blood pump 1. The impeller 12 and pump housing 11 may be made from plastic, metal, ceramic, or similar materials. The pump housing 11 outer diameter may range from 3 mm to 8 mm with a wall thickness ranging from 0.01 mm to 1.0 mm.

An outflow cannula 72 may be provided (see e.g. FIG. 9), which is intended to be placed across one of the heart valves or any artificial valve separating its distal end from its proximal end to create a one way fluid flow through the percutaneous blood pump 1, e.g. from the left ventricle of a patient's heart into the aorta. The outflow cannula 72 may be a self-expanding cannula that grows in diameter during pump operation, to reach three to four times its initial size where it was collapsed around the pump housing 11, typically expanding to a size ranging from 7 mm to 10 mm, preferably 8 mm.

The impeller 12 is attached at its proximal end to a distal flexible cable 27. The distal flexible cable 27 is intended to transmit rotational forces to the impeller 12 to pump any fluid in the contact with impeller 12. The distal flexible cable 27 is housed inside a distal catheter sheath 15 in order to protect surrounding tissue during device operation. The distal flexible cable 27 may be made of single or multiple strands of metallic or plastic wires that are wound together in a fashion to allow the extended operation of the device when placed in a straight or a curved position. The distal catheter sheath 15 is typically made from one or several biocompatible polymeric materials that are intended to resist abrasions to its inner surface resulting from rotation of the distal flexible cable 27 and to resist any contacting blood or bodily fluid deposition on its exterior surface. A lubricating fluid such as saline or similar isotonic intravenous fluid may be contained or pumped through the inner space of the distal catheter sheath 15 in order to reduce abrasion and wear to both the distal catheter sheath 15 and the distal flexible cable 27.

Figure 3:
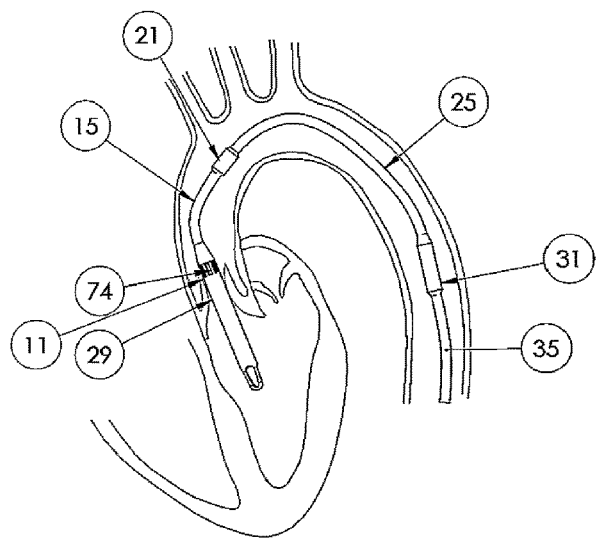
FIG. 3 shows the placement of the first embodiment of the blood pump inside the heart.

As illustrated in FIG. 3, the percutaneous blood pump 1 described herein is designed to be positioned in the left ventricle of a patient's heart to provide augmented arterial circulatory support by generating a non-pulsatile component of flow past the aortic valve into the ascending aorta. The performance of the pump head 10 is a function of the fluid dynamics of the design of the impeller 12 with regards to blade geometry, tip clearance to the inner diameter of the pump housing 11, rotational velocity, and geometry and position of the pump head outflow ports 74. Performance is measured in flow rate as a function of pressure differential between the inflow to the percutaneous blood pump 1 and the outflow. This must be accomplished by minimizing damage to the erythrocytes passing through the percutaneous blood pump 1, caused primarily due to excessive shear imparted to these cells.

Restrictions to the inflow and outflow of the percutaneous blood pump 1 have a significant impact on its performance. It is the intent of the design of the percutaneous blood pump 1 according to the present invention to improve flow characteristics as measured by the factors noted above, by incorporating a transvalvular outflow cannula 72 that, once positioned for operation, is designed to reduce resistance to flow into the aorta by diametral expansion.

The distal edge portion of the pump head's 10 outflow cannula 72 is attached to the pump housing 11 between its distal end at the inflow to the percutaneous blood pump 1, and the pump head outflow ports 74. The following features and aspects of the design are described henceforth. One component of the distal catheter sheath 15 design is its fabrication from a thin-walled biocompatible polymeric tube that presents an atraumatic surface to the margins of the aortic valve with which it comes into cyclic contact. The material used may have elastomeric properties that allow diametric expansion.

The material used may expand by unfolding from a compacted state required for insertion and positioning, into the larger size employed during pump operation. The unfolding and diametral expansion of the distal catheter sheath 15 may be activated by the outflow pressure generated by the percutaneous blood pump 1 itself.

The material used may be coated with a lubricious, possibly hydrophilic coating, to enhance intraoperative insertion and reduce friction on the leaflet margins of the aortic valve. The material used may be required to conform closely to the pump head 10 and distal catheter during insertion.

Another component of the distal catheter sheath 15 may be the incorporation of a reinforcement material in the wall of the polymeric tube of the distal catheter sheath 15. These reinforcements 79 (see FIG. 9) provide for shape definition and retention, size adjustment during deployment, and kink resistance.

The reinforcement material may be a biocompatible metallic wire alloy such as stainless steel, or a fiber, such as a polymeric or carbon. The reinforcement may be a shape-memory metal such as Nitinol to provide the distal catheter sheath 15 with the ability to self-expand based on the elevated temperature encountered intraoperatively in the patient or with super elasticity to self-expand once a confining sheath is retracted away from the distal catheter sheath 15. The embedded reinforcement may be wound circumferentially around the tube wall and may have a tapered configuration with the larger diameter at the proximal end of the cannula allowing a twisting action of expansion when employed with an elastomeric-type polymer. A memory metal type wire reinforcement would be applicable in such an embodiment. The embedded reinforcement may be arranged as multiple straight longitudinal elements along the length of the cannula to provide tapered expansion from the distal attachment at the pump housing 11 to the proximal end of the distal catheter sheath 15 at the outflow into the aorta. This would be suitable to the foldable embodiment described above and use of a memory metal for reinforcement would be applicable. These longitudinal cannula reinforcements 79 may be extended to attach to a sliding annular ring 80 (see FIG. 9) around the distal catheter sheath 15 that provide a method for sliding a mechanical containment cover over the outflow cannula 72 to facilitate the insertion and extraction of the device when in the compressed state. The annular ring 80 may be detachable and (re-)attachable.

Figure 6A:
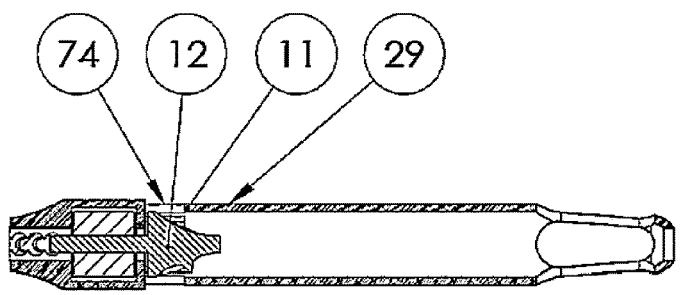
FIG. 6A shows a detailed lateral section view of the distal housing shown in FIG. 6.
Figure 6:
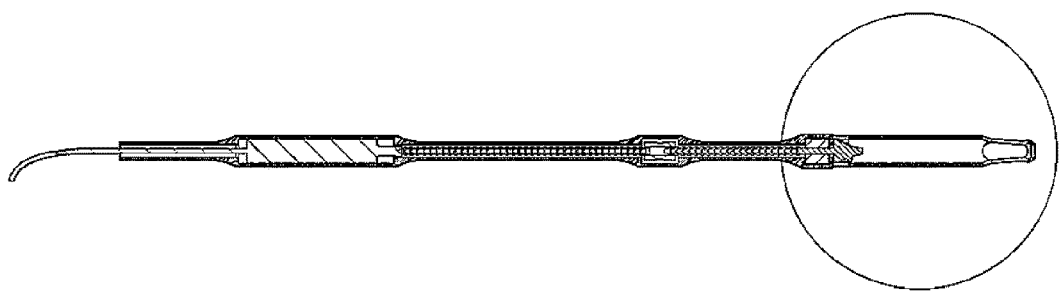
FIG. 6 shows a lateral section view of the pump head of segmented blood pump with mechanical coupling.

Again referring to the embodiment shown in FIGS. 1 to 3, the percutaneous blood pump 1 comprises three distinct housings 11, 21, 31 connected by means of a flexible cable or a solid shaft that is rotated inside a protective flexible sheath. The most distal housing, the pump housing 11, houses the impeller 12 and possibly a set of radial and axial bearings intended to center the impeller 12 inside the pump housing 11 during operation. An inflow cannula 29 is located on the distal end of the pump housing 11 to provide a port for drawing the blood into the percutaneous blood pump 1. Likewise, a pump head outflow port 74 is located on the proximal end of the pump housing 11 for directing the blood which has been drawn in through the inflow cannula 29 by the impeller 12 into the aorta and the rest of the patient's body. See also FIGS. 6 and 6A.

The middle or bearing housing 21, houses a bearing set 22 that includes axial and possibly radial bearings, and act as the main bearings for proper function of the impeller 12. The bearing set 22 takes the axial and radial loads introduced by an electric motor 30 and middle flexible cable 26 linking electric motor 30 to the bearing set 22; therefore, isolating the impeller 12 from any excessive axial or radial forces exerted by the electric motor 30, the middle flexible cable 26 or any other axially exerted force in the system. Therefore, heat generated at the pump head 10 and the pump housing 11 is reduced to a minimal level. Heat reduction in the pump head 10 area may reduce any clotting in the percutaneous blood pump 1 and, therefore, extend device life. Either a single or multitude solid, semi solid, and/or flexible cable transmits the rotation of the electric motor 30 to any rotating elements in the bearing housing 21 and pump head 10 to rotate the impeller 12. The flexible cable could be made from metallic, polymeric, fibrous, mechanically linked elements or a combination of several different materials.

The proximal or motor housing 31, houses a small diameter electric motor 30 that is powered by electricity delivered by electric wires 36, housed inside a proximal catheter sheath 35 that links the motor housing 31 to the outside of the patient body. The distal catheter sheath 15 and middle catheter sheath 25 are single or multi-lumen sheaths that serve to isolate the distal flexible cable 27 and the middle flexible cable 26 from contacting patient tissue, to center the associated rotating the distal flexible cable 27 and the middle flexible cable 26, and to serve as conduit to deliver or remove fluid and/or debris toward or away from the pump head 10. A lubricating fluid such as saline or similar isotonic intravenous fluid may be circulated inside the distal catheter sheath 15, middle catheter sheath 25, and proximal catheter sheath 35. The lubricating fluid can be circulated by means of a typical peristaltic or piston pump (not shown) placed outside the patient body.

Figure 4:
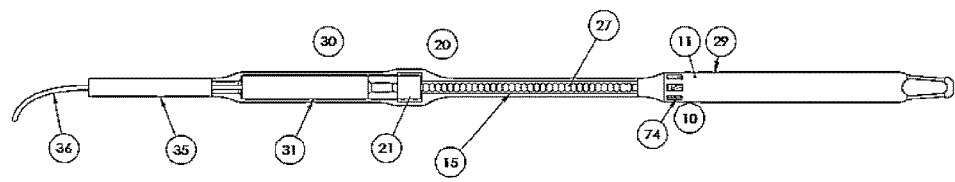
FIG. 4 shows a lateral partial sectional view of a second embodiment of the segmented blood pump.

In another embodiment, shown in FIG. 4, the percutaneous blood pump 1 comprises two distinct housings connected by means of a flexible cable and/or a solid shaft that is rotated inside a protective flexible sheath. It is also referred to the description of the embodiment of FIG. 1 for corresponding components. The most distal or pump housing 11 houses the impeller 12 and may house a set of magnets to form a magnetic coupling between the impeller 12 and the distal flexible cable 27 as well as a set of radial and possibly axial bearings intended to center the impeller 12 and/or the coupling magnets inside the pump housing 11 during operation. The proximal housing or motor housing 31 comprises a set of axial and radial bearings and a set of coupling magnets that act as the main bearings for the impeller 12 proper functioning as well as the electric motor 30. The bearing set 22 basically takes the axial and radial loads introduced by the electric motor 30 and may be cooled by any means. Therefore, the impeller 12 is isolated from any excessive axial or radial forces exerted by electric motor 30, flexible cable, solid shaft, or any other element in the system. Therefore, heat generated at the pump housing 11 is reduced to a minimal level, which may reduce any clotting in the pump housing and, therefore, to extend device life as described above. The distal catheter sheath 15 is single or multi-lumen sheath that serves to isolate the associated rotating cable from contacting patient tissue, to center the associated rotating flexible cable, and to serve as conduit to deliver or remove fluid and/or debris toward or any from pump head 10. A lubricating fluid such as saline or similar isotonic intravenous fluid may be circulated inside distal catheter sheath 15. The lubricating fluid may be circulated by means of a typical peristaltic or piston (not shown) placed outside the patient body.

Figure 5:
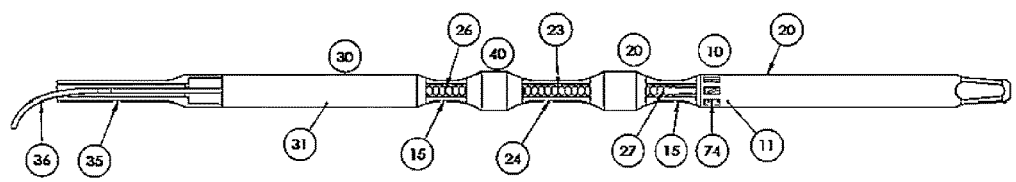
FIG. 5 shows a lateral partial sectional view of a third embodiment of the segmented blood pump with the magnetic motor and bearing separated.
Figure 7:
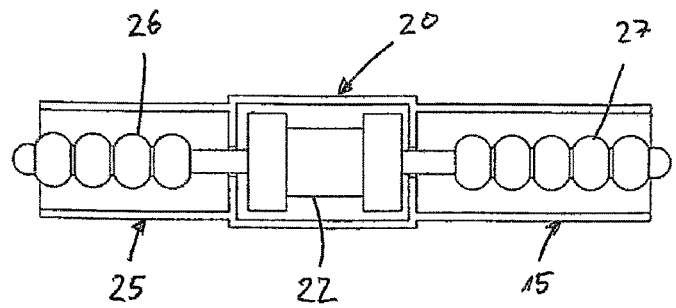
FIG. 7 shows a lateral sectional view of the bearing.
Figure 7A:
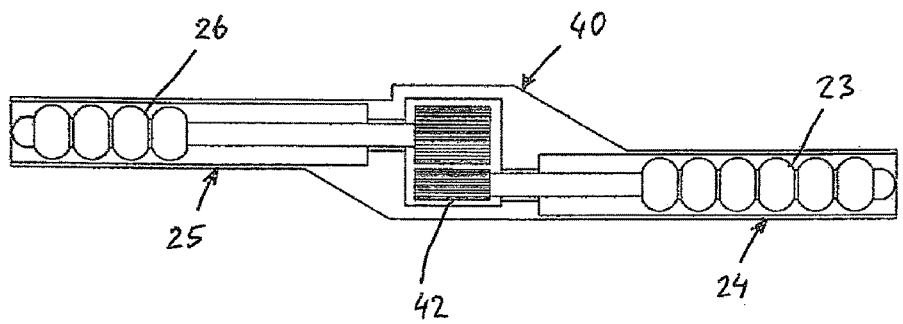
FIG. 7A shows a lateral sectional view of a gear.

In still another embodiment, shown in FIG. 5 and similar to the embodiments of FIGS. 1 and 4, rotation caused by the electric motor 30 is not directly transferred to the rotating impeller 12. Rather, a gear box 40 is inserted in between the electric motor 30 and the bearing 20 in order to increase or decrease the rotational speed of the percutaneous blood pump 1, more specifically the rotational speed of the impeller 12, by means of a gearing mechanism 42. The gearing mechanism 42 may comprise planetary gears that are co-axial and therefore may have a smaller overall diameter. The gear box 40 is further shown in more detail in FIG. 7A, while the bearing 20 without a gearing mechanism is shown in FIG. 7. The rotation of the electric motor 30 is transferred from the gear box 40 to the bearing 20 by means of a flexible cable or shaft 23 inside a catheter sheath 24. The flexible cable or shaft 23 may be made as described for the cables 26 and 27. For further components of the embodiment of FIG. 5, it is referred to the corresponding description of the embodiment of FIG. 1 and FIG. 4.

Figure 8:
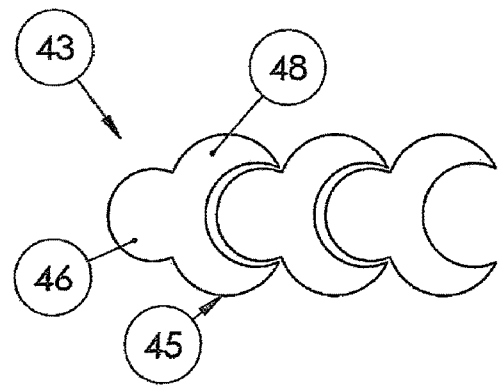
FIG. 8 shows a second embodiment of the blood pump flexible cable.
Figure 8A:
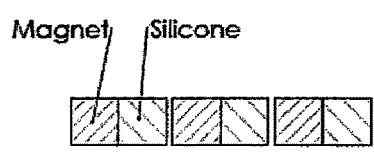
FIG. 8A shows a third embodiment of the blood pump flexible cable.
Figure 8B:
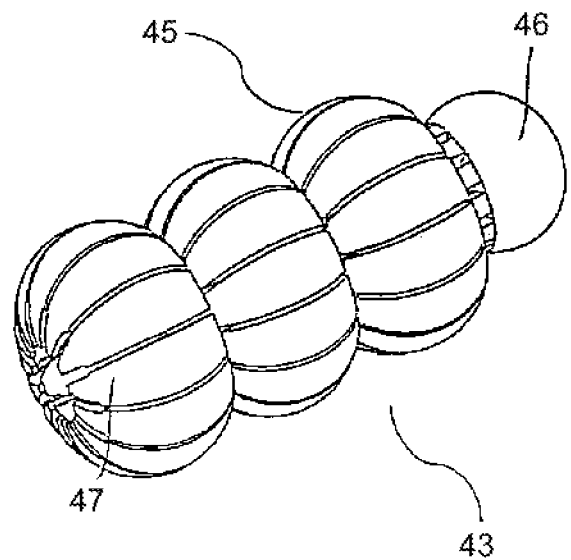
FIG. 8B shows the snap elements fitted together to form the blood pump flexible cable.
Figure 8C:
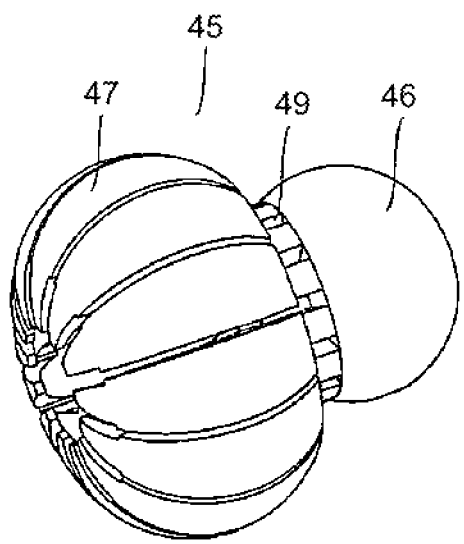
FIG. 8C shows a detailed view of a snap element.
Figure 8D:
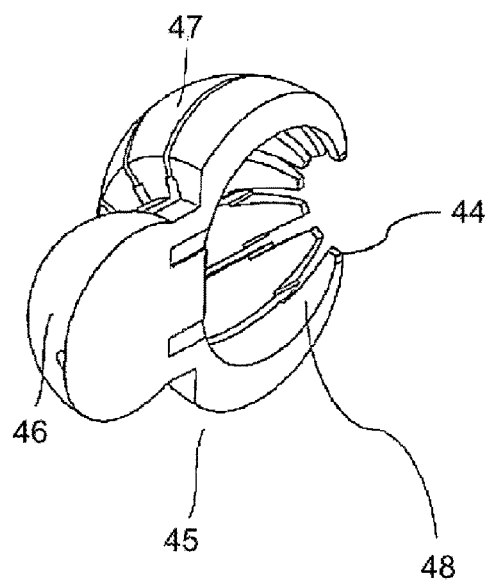
FIG. 8D shows a sectional view of a snap element.

Any of the flexible cables 23, 26, 27, 36 could be made from multi-wires wound together to form single or multiple layers as described e.g. in U.S. Pat. No. 7,828,710. Alternatively, any of the flexible cables 23, 26, 27, 36 may be made of a series of snap elements 45 that are fitted together to form snap drive cable 43 as shown in FIG. 8. The snap elements 45 may have a ball 46 that snaps and mechanically locks during rotation inside another snap element's cup 48. Two consecutive snap elements 45 lock during rotation by having a locking tip 44 of one snap element 45 mechanically engaging a locking groove 49 of another snap element 45 as illustrated in FIGS. 8B, 8C and 8D. The extent of force of engagement of the locking tip 44 and locking groove 49 determines the maximum torque the snap drive cable 43 can transmit before the locking tip 44 mechanically disengages from the locking groove 49. Limiting the maximum torque that the snap drive cable 43 can transmit reduces the risk associated with existing drive cables. Existing drive cables can transmit a very high torque and in case of device malfunction the cable will continue to rotate with the potential of perforating its protective sheath and ultimately causing severe damage to surrounding tissue and possibly patient's death. In another embodiment, as shown in FIG. 8A, the cable elements could be made to connect to each other via a magnetic coupling or a magnetic coupling in addition to the mechanical snap elements. A drive cable made from snap element 45 would allow a greater curvature than existing wire wound drive cable without the risk of failure or wear. In a further embodiment, a flexible cable could be made from a combination of sections of wound wire, mechanical snapping elements 45, and/or magnetically locked elements. The location and number of such sections could be designed to fit the design requirement wherein each section is selected based on the dynamic requirement of torque transmission in that section. For example, in the section where the cable is in a straight position a wire wound cable could be used and in a curved section a "snap element" design could be used. It will be appreciated that any of the above described embodiments of a percutaneous blood pump 1, e.g. with two or three distinct housings, may be combined with any of the described types of flexible cables.

In an embodiment, specifications as described above are the same, but the percutaneous blood pump 1 with three distinct housings can be alternately connected by means of mechanically linked elements that are rotated inside the protective flexible sheath. The bearing set 22 then takes the axial and radial loads introduced by electric motor 30 and the mechanically linked elements linking electric motor 30 to the bearing set 22; therefore isolating the impeller 12 from any excessive axial or radial forces exerted by electric motor 30, the mechanically linked elements or any other axially exerted force in the system. A combination of solid, semi solid, and/or flexible cables, and mechanically linked elements transmit the rotation of electric motor 30 to any rotating elements in bearing housing 21 and pump head 10 to rotate the impeller 12.

In another embodiment, specifications are the same as described above, but the percutaneous blood pump 1 with three distinct housings can be alternately connected by means of magnetically or mechanically linked elements that are rotated inside the protective flexible sheath. The bearing set 22 then takes the axial and radial loads introduced by electric motor 30 and the magnetically or mechanically linked elements linking electric motor 30 to the bearing set 22; therefore isolating the impeller 12 from any excessive axial or radial forces exerted by electric motor 30, the magnetically or mechanically linked elements or any other axially exerted force in the system. A combination of solid or semi solid magnetically or mechanically linked elements transmit the rotation of electric motor 30 to any rotating elements in bearing housing 21 and pump head 10 to rotate the impeller 12.

In another embodiment, specifications are the same as described above, but the percutaneous blood pump 1 with three distinct housings can be alternately connected by means of a flexible cable and/or a solid shaft that are rotated inside the protective flexible sheath. The most distal housing, pump housing 11, houses the impeller 12 and a set of magnets to form a magnetic coupling between the impeller and the drive shaft as well as a set of radial and possibly axial bearings intended to center the impeller 12 and/or the coupling magnets inside the pump housing 11 during operation. The bearing set 22 basically takes the axial and radial loads introduced by electric motor 30 and the flexible cable linking the electric motor 30 to the bearing. Therefore, isolation of the impeller 12 from any excessive axial or radial forces exerted by electric motor 30, flexible cable, solid shaft, or any other element in the system is achieved. Therefore, heat generated at the pump housing 11 is reduced to a minimal level. Heat reduction in the pump housing 11 area is well known to reduce any clotting in the pump and, therefore, to extend device life. Magnetic coupling could be used in any connection along the path of cable rotation starting with the connection between electric motor 30 and middle flexible cable 26 transmitting electric motor 30 rotation to bearing set 22, the connection between middle flexible cable 26 and bearing set 22, the connection between the bearing set 22 and distal flexible cable 27 transmitting torque to pump head 10, or between distal flexible cable 27 and pump head 10 transmitting torque to impeller 12.

In yet another embodiment, the percutaneous blood pump 1 may comprise two distinct housings connected by means of a flexible cable and/or a solid shaft that is rotated inside a protective flexible sheath. The flexible cable and/or solid shaft could be "very short", relative to the distance from the pump housing 11 all the way to the exterior of the patient, ranging from 1 mm to 150 cm preferably between 4 mm and 4 cm. The separation of the pump housing 11 from the electric motor 30 would distance the heat generated by the electric motor 30 as compared to that generated if the blood pump and the motor were in close proximity that is responsible for any clotting and blood damage. In addition, in the left ventricle support situation, the "very short" cable will tend to be in a straight configuration occupying the section of the left ventricle and ascending aorta. Operating any driver cable in a straight geometry will extend the drive cable life, reduce any possible wear, reduce heat generation, and reduce power required from the electric motor 30 to operate the device. Having a reduced bearing and drive cable temperature will allow the operation of the device with or possibly without the need of any lubricant intended to continually wash the bearing as described in U.S. Pat. No. 5,911,685. In addition, the short drive cable will increase its life span significantly since the effect of the cyclical loading and unloading is decreased to the point that it does not cause significant wear as was observed on earlier drive cable design. Also, the separation of the pump housing 11 from the bearing and electric motor 30 reduce the overall length of the solid length of the device and therefore allow the ease of device insertion and curvature negotiation.

Figure 9:
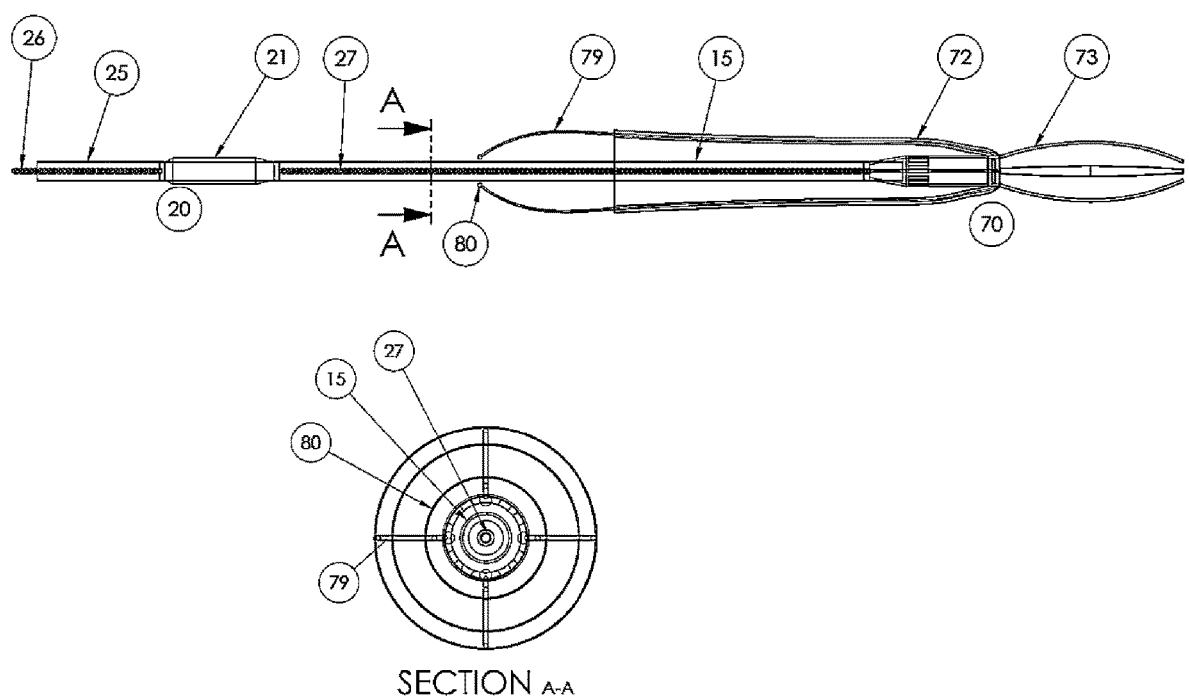
FIG. 9 shows a lateral view of a fourth embodiment of a segmented blood pump with ventricular pump head.
Figure 10:
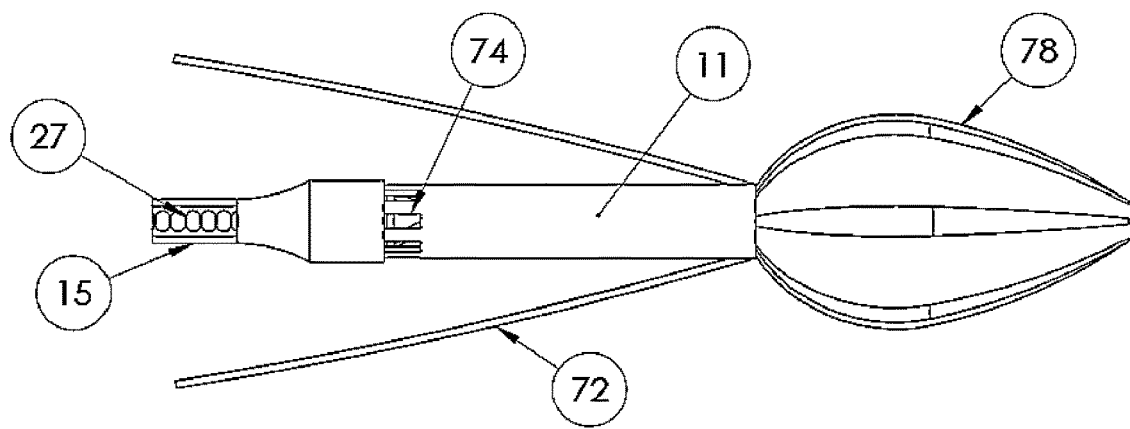
FIG. 10 shows a lateral view of a fifth embodiment of a segmented blood pump with ventricular pump head and sensors.
Figure 11:
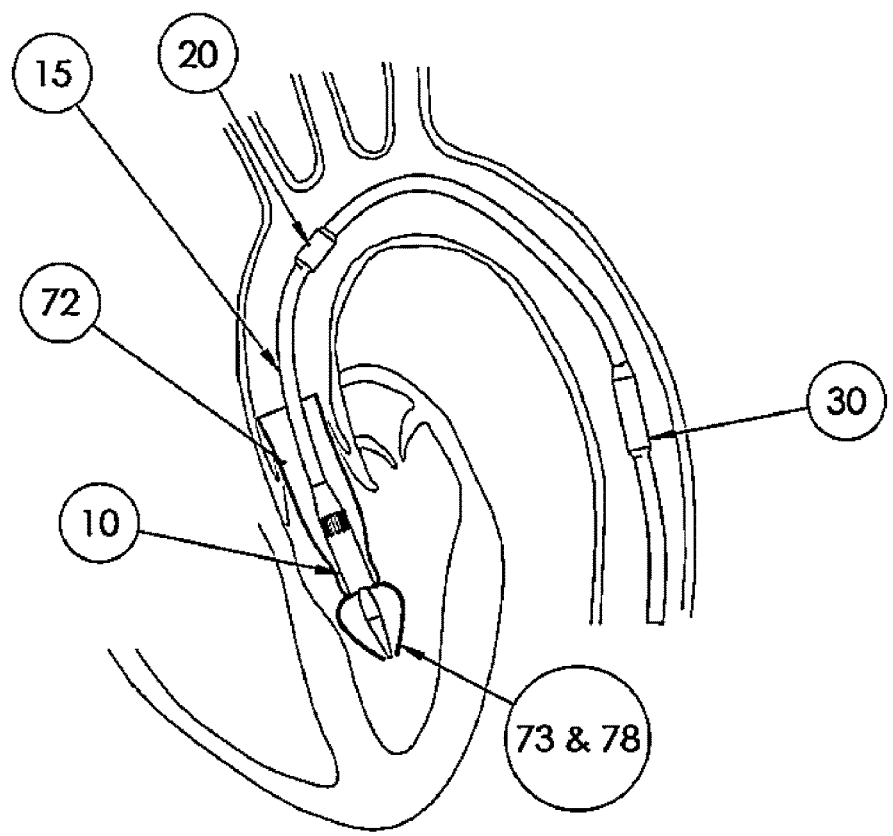
FIG. 11 shows the placement of the blood pump inside the heart.

As shown in FIGS. 9, 10 and 11, the most distal or pump housing 11 can also comprise a single or a set of "fingers" extend beyond the distal end of pump housing 11 and form a pump head sensor cage 78 that keeps the inflow to the pump 1 away from surrounding tissue to reduce the chance of tissue sucked into impeller 12. In addition, the pump head sensor cage 78 function as a sensor sensing the position of the individual "fingers" and therefore the distance of pump housing 11 from the surrounding tissue, the contraction phase of the ventricle, relative or absolute ventricular volume, the speed of ventricular contraction, the ejection fraction of the ventricle, the location of any localized infracted myocardium, and the EKG of the heart. The pump head sensor cage 78 may be designed to provide the point-of-care team of physicians with information on the pump's performance and indicators of the patient's condition and level of circulatory support. To achieve this, the pump head sensor cage 78 may incorporate sensors that may transmit signals via wires and/or wirelessly via radio frequencies (RF) to an external control unit that may utilize embedded firmware algorithms to produce useful clinical information. Placement and types of sensors are dependent on the priority placed on the parameters considered most critical to the monitoring physician. The sensors will typically utilize micro electromechanical machine (MEMS) technology but can also be comprised of strain gage and/or ultrasonic/piezoelectric type sensors, or simple electrodes, and produce outputs that can include pressure, force, proximity, or electrical signals. One or more of these sensors may be positioned on the inflow cannula 29 in the left ventricle, likely on the tip, with an additional pressure sensor in the aorta integrated into the outflow cannula 72. The signals transmitted from force and proximity transducers could be processed to provide positioning information and/or left ventricular volume to calculate left ventricular ejection fraction (LVEF). The differential pressure between to pump's inlet and outlet can be used to determine a continuous measure of blood flow dynamically during the systole/diastole cardiac cycle coupled with mean arterial pressure MAP that is typically monitored intraoperatively. This would be achieved by using an algorithm based on the Bernoulli and Hagen-Poiseuille equations. Outputs from this could include mean total blood flow LPM or as augmented flow produced by the pump's assist. The proximal housing comprises a set of axial and radial bearings and a set of coupling magnets that act as the main bearings for the impeller proper functioning.

According to another aspect of the disclosure, an introducer system is provided, which may be configured for insertion of any of the above described percutaneous blood pumps 1 into a patient's vessel, such that the blood pump 1 can be advanced through the circulatory system into the patient's heart. Embodiments of the introducer system are shown in FIG. 12 to FIG. 23 and will be described hereinafter.

Figure 12:
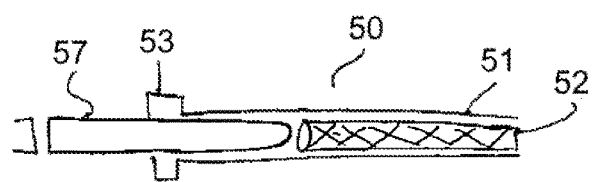
FIG. 12 shows an embodiment of an introducer system.
Figure 13:
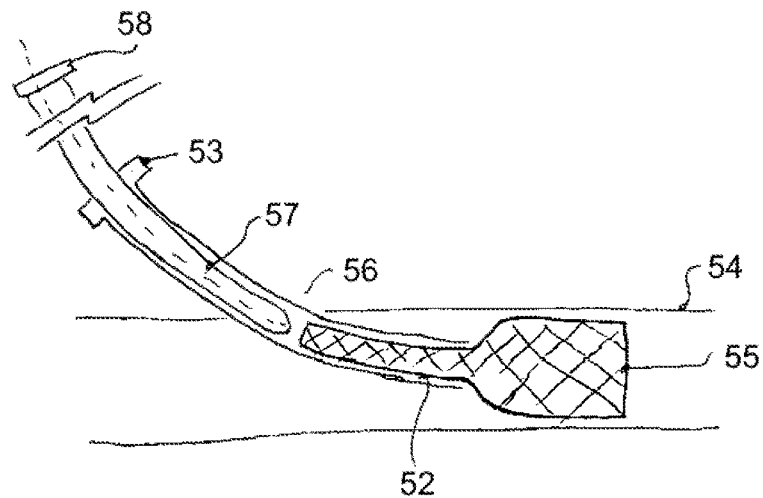
FIG. 13 shows deployment of the embodiment of an introducer system.
Figure 14:
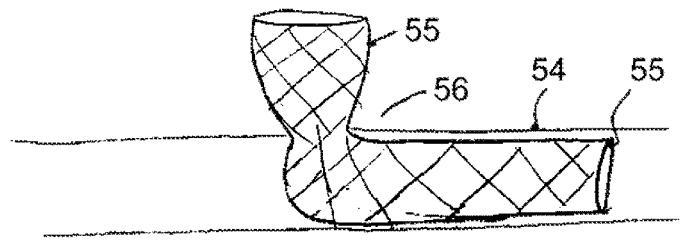
FIG. 14 shows the embodiment of the introducer system deployed.

As shown e.g. in FIGS. 12 to 14, an introducer system may be provided as an expandable introducer set 50 that comprises an expandable structure 52, a dilator 57, an insertion sheath 51, and a vessel dilating balloon catheter 59. The expandable structure 52 may be a tubular metallic structure such as nitinol, or polymeric structure that self-expands or is expanded by means of a balloon that is inflated inside expandable structure 52 to cause a permanent deformation and expansion of expandable structure 52. The dilator 57 may be a cylindrical tubular structure with a central lumen, intended to receive a standard guide wire, with a tapered distal end that extends distally and proximally of the expandable structure 52 during introduction of the introducer set 50 into the patient. The insertion sheath 51 may be a tubular thin walled polymeric tube that receives the expandable structure 52 in its compressed form and the dilator 57 to form a single cylindrical structure that may be inserted as a unity into the patient's vessel possibly advanced over a pre-positioned guide wire position using Seldinger technique. The insertion sheath 51 may be "peel-away" type, and may be peeled while inside the patient vessel therefore freeing the expandable structure 52 to expand due to its inherent design or by the action of an inner balloon when inflated causing a force to be exerted on the inner surface of the expandable structure 52 and ultimately causing it to expand to a defined diameter. The compressed expandable structure 52 outer diameter could range from 1 mm to 4 mm preferably from 2 mm to 3 mm, while its expanded diameter could range from 3 mm to 10 mm preferably from 4 mm to 8 mm.

Figure 15:
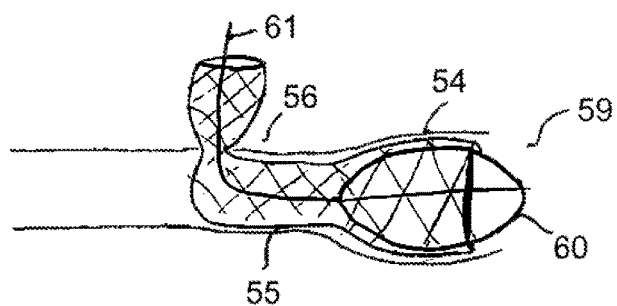
FIG. 15 shows the embodiment of the introducer system with further diameter expansion.

In one embodiment shown in FIG. 15, a vessel dilating balloon catheter 59 comprises a catheter and dilating balloons 60. The catheter may range in diameter from 0.5 mm to 3 mm with an inner lumen through its entire length to allow the passage of a standard guide wire and a minimum of one dilating balloon at its distal end in communication with the proximal end of the vessel dilating balloon catheter 59 by means of a separate lumen adjacent to the inner lumen which allows the passage of fluid to inner balloon space to cause the balloon inflation or deflation. The dilating balloon 60 could be either a compliant or non-compliant thin polymer that matches the inner wall of the patient vessel and could range in length from 1 cm to 20 cm long preferably 5 cm to 10 cm in length. The vessel dilating balloon catheter 59 may have a single or multiple dilating balloons 60 at the distal end of the vessel dilating balloon catheter 59 that inflate simultaneously, in sequence, or in an order selected by the user that suits the nature of the vessel that is being treated. In the case where more than one dilating balloon 60 are mounted to the distal end of vessel dilating balloon catheter 59, one lumen or a multitude of separate lumens connect each inner space of a dilating balloon 60 to the proximal end of vessel dilating balloon catheter 59 via a separate inflation port could be used to inflate individual or all dilating balloons 60.

Figure 16:
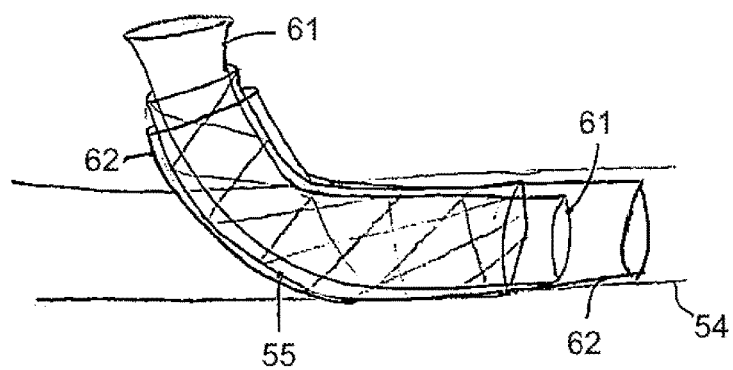
FIG. 16 shows another embodiment of an introducer system deployed.

In another embodiment of the introducer set as shown in FIG. 16, specifications are the same as above, but the expandable introducer set 50 can alternately be comprised of an expandable structure 52, an inner liner 61, a dilator 57, an insertion sheath 51, an outer liner 62, and a vessel dilating balloon catheter 59. The inner liner 61 lines the inner surface of the expandable structure 52, and is a thin polymeric jacket that allows the passage of any device with ease. the inner liner 61 is attached to the expandable structure 52 inner surface, free floating, or attached only at the proximal and distal ends of expandable structure 52. The inner liner 61 may be coated with a lubricous coating that facilitates the slippage of any device inside the expandable structure 52. The outer liner 62 lines the outer surface of the expandable structure 52 and abuts the inner wall of the vessel 54 used for device introduction. The outer liner 62 could be made from a variety of polymeric materials such as but not limited to Dacron, PTFE, or polyamide. The outer liner 62 is attached to the expandable structure 52 outer surface, free floating, or attached only at the proximal and distal ends of the expandable structure 52.

Figure 17:
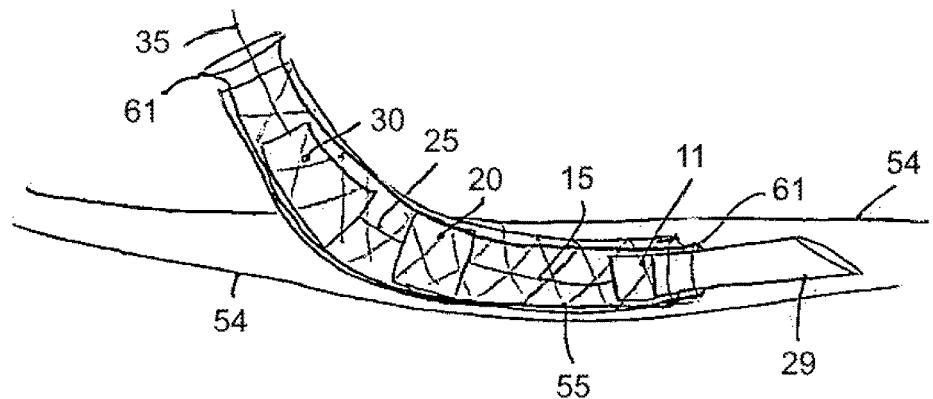
FIG. 17 shows pump advancement into the deployed introducer system.

In another embodiment of the introducer set as shown in FIG. 17, specifications are the same as above, but the expandable introducer set 50 can alternately be comprised of an expandable structure 52, an inner liner 61, a dilator 57, an insertion sheath 51, and a vessel dilating balloon catheter 59. An inner liner 61 lines the inner surface of the expandable structure 52, and is a thin polymeric or non-polymeric jacket ranging in thickness from 0.001 mm to 0.5 mm that allows the passage of any device with ease. The inner liner 61 is attached to the expandable structure 52 inner surface, free floating, or attached only at the proximal and distal ends of expandable structure 52. The inner liner 61 may be coated with a lubricous coating that facilitates the slippage of any device inside the expandable structure 52. Apart from that, FIG. 17 illustrates the introducer set with a blood pump 1 deployed.

Figure 18:
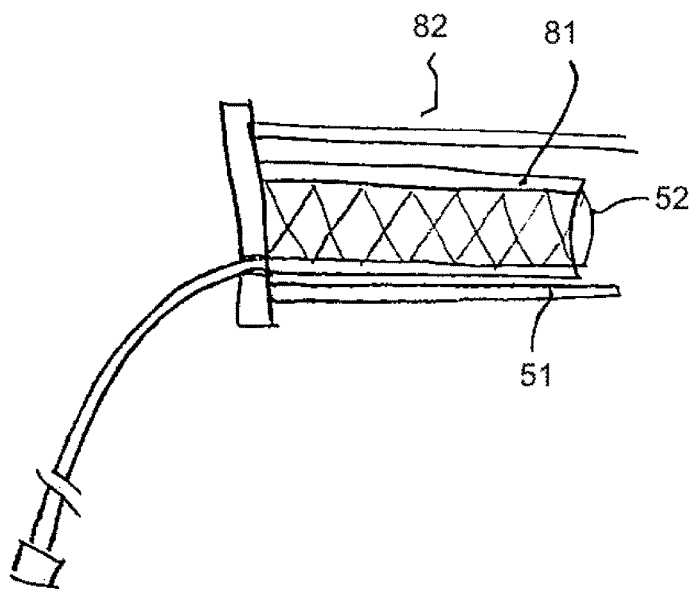
FIG. 18 shows an embodiment of the introducer system with integrated balloon.
Figure 19:
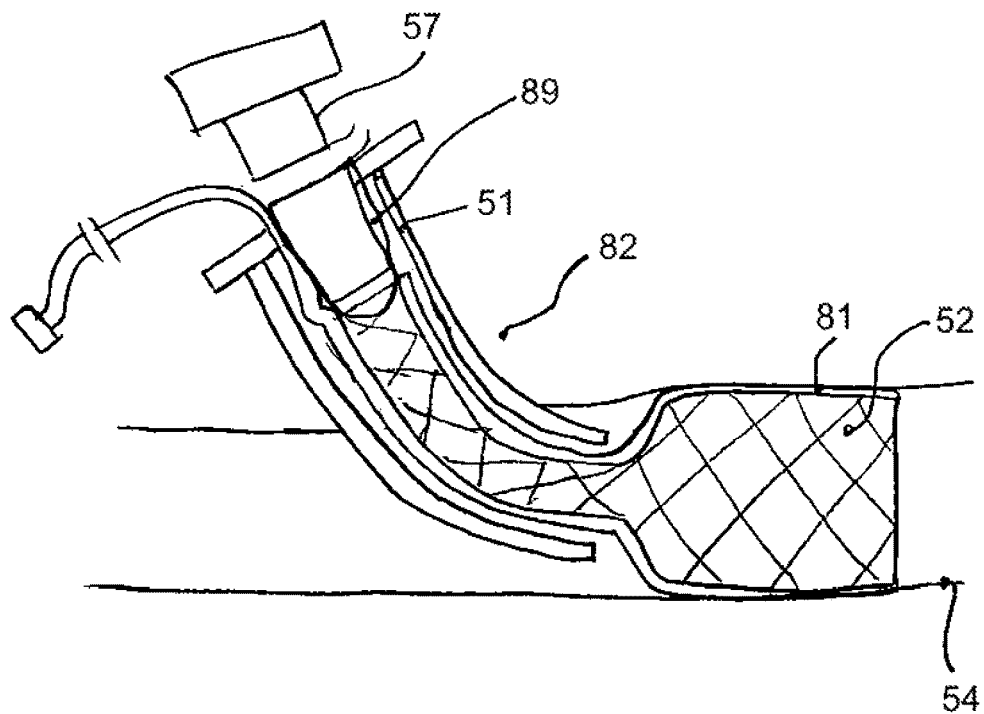
FIG. 19 shows the embodiment of the introducer system with integrated balloon deployed.
Figure 20:
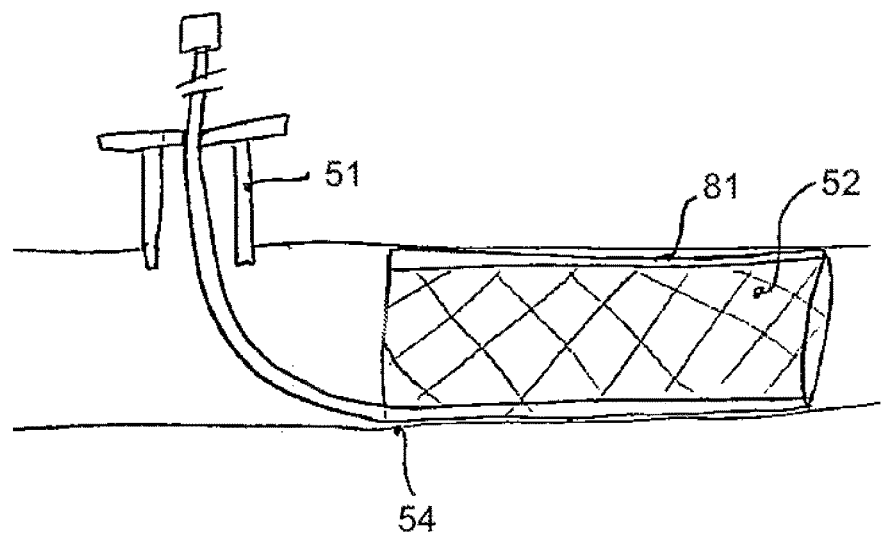
FIG. 20 shows the introducer system with integrated balloon deployed in a vessel.
Figure 21:
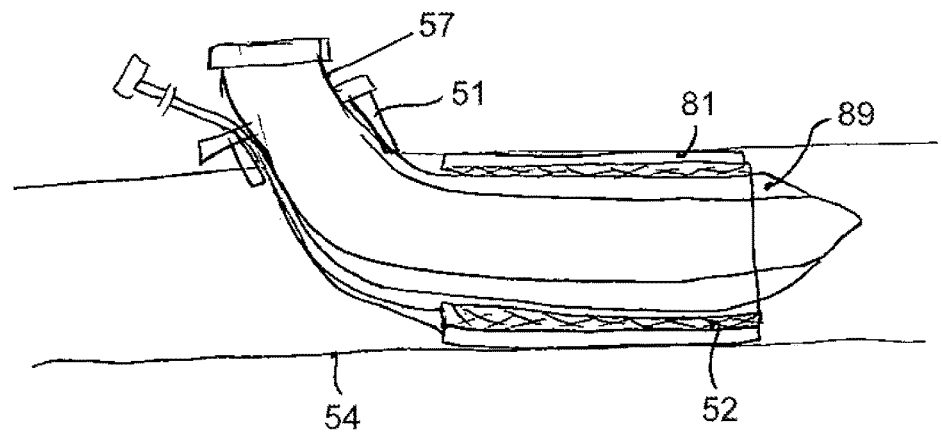
FIG. 21 shows dilator advancement into the deployed introducer.
Figure 22:
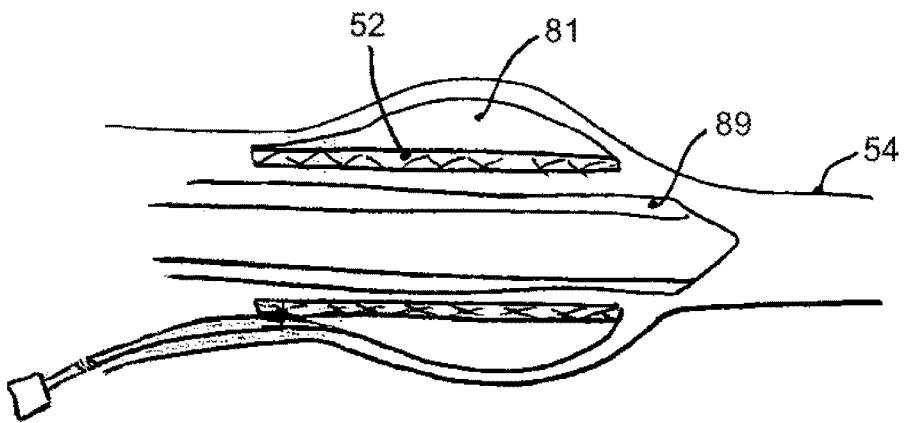
FIG. 22 shows an embodiment of an introducer system with integrated balloon inflated inside an expandable structure.
Figure 23:
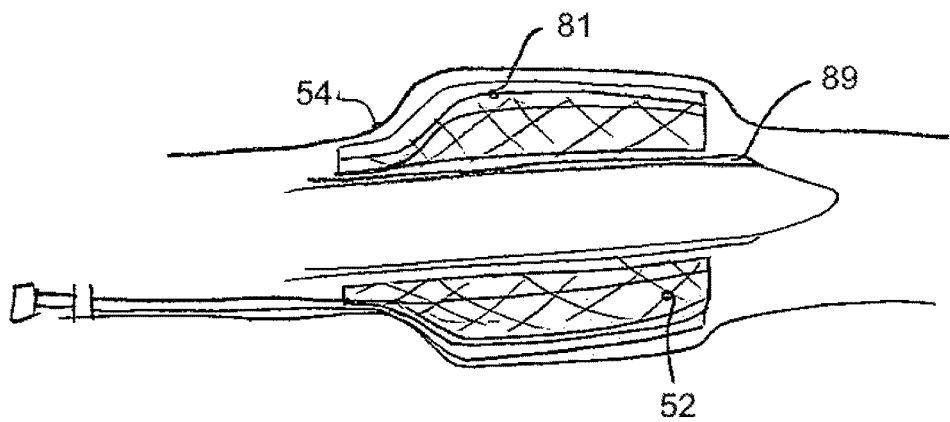
FIG. 23 shows expansion of the expandable structure caused by outer balloon inflation.

In another embodiment as shown in FIGS. 18 to 20, an expandable introducer with an integrated balloon set 82 is provided, which comprises an expandable structure 52, a dilator 57, an insertion sheath 51, a dilator balloon catheter 89 and an outer balloon 81. The expandable structure 52 may be a tubular metallic, such as nitinol, or polymeric structure that self-expands or is expanded by means of a balloon that is inflated inside the expandable structure 52 to cause a permanent deformation and expansion of the expandable structure 52. The outer balloon 81 is attached to the expandable structure 52 outer surface, free floating, or attached only at the proximal and distal ends of the expandable structure 52. The outer balloon 81 may be made from a variety of polymeric materials such as PTFE, nylon, silicone, or polyamide and could be stretchable or nonstretchable, therefore could be inflated to a maximum specified diameter. The dilator 57 may be a cylindrical tubular structure with a central lumen, intended to receive a standard guide wire, with a tapered distal end that extends distally and proximally of the expandable structure 52 during introduction of the introducer set 50 into the patient. The dilator balloon catheter 89 may be mounted on the outside surface of the dilator 57 and inflated after expandable structure 52 is expanded to provide inner support to the expandable structure 52. The insertion sheath 51 may be a tubular thin walled polymeric tube that receives the expandable structure 52 in its compressed form and the dilator 57 to form a single cylindrical structure that could be inserted as a unity into the patient vessel possibly advanced over a pre-positioned guide wire position using Seldinger technique. The insertion sheath 51 may be "peel-away" type, and may be peeled while inside the patient vessel therefore freeing the expandable structure 52 to expand due to its inherent design or by the action of an inner balloon when inflated causing a force to be exerted on the inner surface of the expandable structure 52 and ultimately causing it to expand to a defined diameter. The compressed expandable structure 52 outer diameter may range from 1 mm to 4 mm, preferably from 2 mm to 3 mm, while its expanded diameter may range from 3 mm to 10 mm, preferably from 4 mm to 8 mm. After the expandable introducer with integrated balloon set 82 is positioned inside the target vessel further vessel dilation could be done using the outer balloon 81. The outer balloon 81 may be inflated while the dilator balloon catheter 89 is inflated to provide support to the expandable structure 52 therefore dilating the target vessel rather than compressing the expandable structure 52. A single dilation or successive dilations could be used to dilate small section or the entire length of the target vessel. The outer balloon 81 and/or dilator balloon catheter 89 may be made of a single or multiple compartments that could be inflated simultaneously or separately to affect one or several areas of the targeted vessel. The outer balloon 81 dilation is basically to expand the expandable introducer with integrated balloon set 82 in a constricted area or the entire length of the target vessel that might interfere with device introduction.

Any of the expandable introducers mentioned above may have the expandable structure 52, inner liner 61, and/or outer liner 62 made from a tubular polymeric structure that is non-biodegradable or biodegradable materials that may be used as a permanent implant. In the case where the material is biodegradable, the expandable structure 52, inner liner 61, and/or outer liner 62 may degrade with time. Alternatively or in addition, the expandable structure 52, inner liner 61, and/or outer liner 62 may be impregnated with different kind of drugs, such as anti-inflammatory drugs that will reduce any inflammation due to the deployment and manipulation of introducer or any of its components, or drugs that will enhance the healing of the vessel wall, or drugs that will reduce the chance of thrombus deposits on the vessel wall in the area that is affected by the introducer deployment.

A closure device 51 as shown in FIG. 20 may be part of the introducer system. The closure device 51 allows vessel closure without the need to surgically repair the vessel. This is done with a pull wire from the opposite leg or an opposite opening (not shown).

Figure 24:
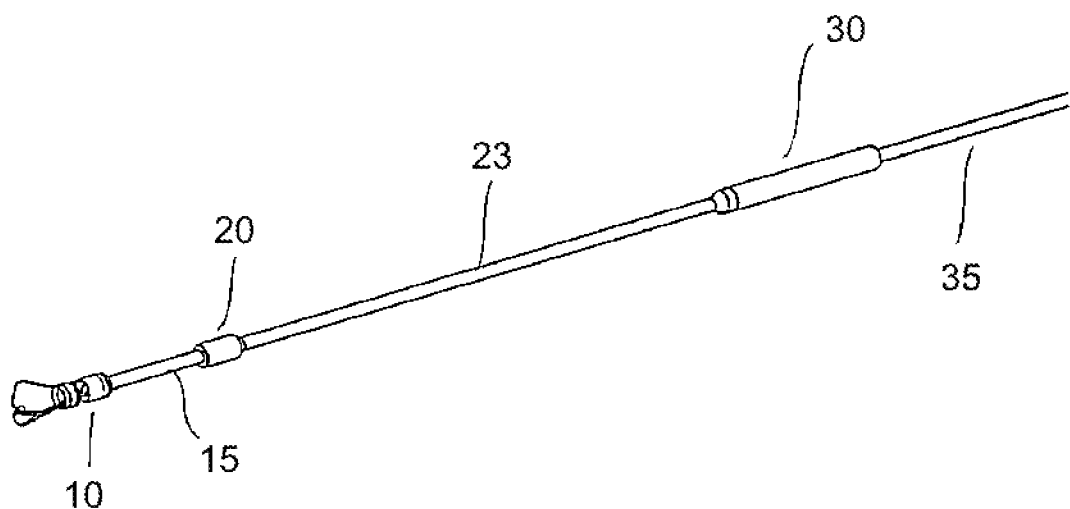
FIG. 24 shows a perspective view of an embodiment of a percutaneous blood pump.
Figure 25:
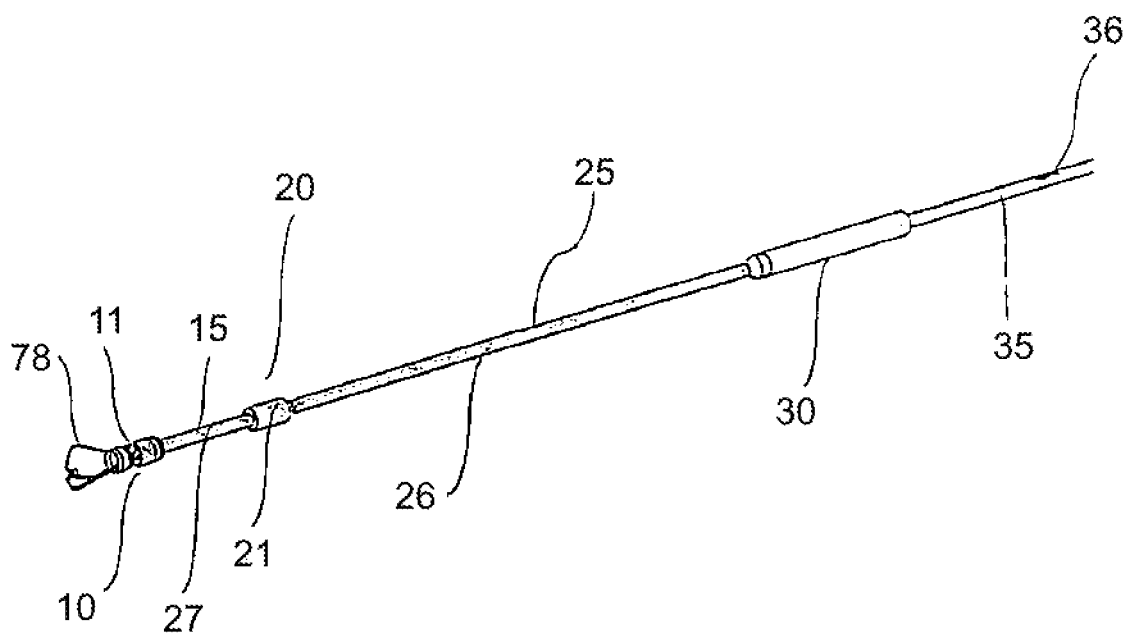
FIG. 25 shows a perspective view of an embodiment of a percutaneous blood pump.
Figure 26:
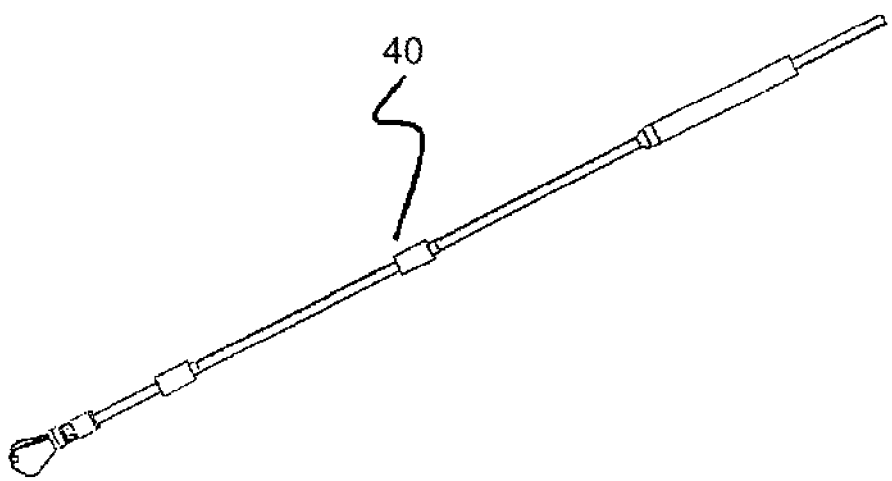
FIG. 26 shows a perspective view of an embodiment of a percutaneous blood pump.

FIGS. 24 to 26 show perspective views of a percutaneous blood pump 1 in accordance with further embodiments similar to those shown in FIG. 1 and FIG. 5, respectively. Thus, it is referred to the detailed description above.

It will be appreciated that any of the above described embodiments of a percutaneous blood pump may be used with any embodiment of the above described introducer sets. Further, any component of the embodiments of the percutaneous blood pump may be used alone or in combination with any of the other embodiments of the percutaneous blood pump without departing from the scope of the invention. Likewise, any component of the embodiments of the introducer set may be used alone or in combination with any of the other embodiments of the introducer set without departing from the scope of the invention.

The invention claimed is:

1. A percutaneous blood pump for percutaneous insertion into a patient's circulatory system, the blood pump comprising a pump housing with an impeller housed in the pump housing, the impeller being rotatable so as to cause blood to be drawn into and through the pump housing, and a motor housing an electric motor for causing a rotational movement, the motor housing being distinct from the pump housing and spaced apart from the pump housing in a proximal direction, the blood pump further comprising at least one flexible sheath extending between the motor housing and the pump housing and at least one flexible cable extending through the flexible sheath so as to transfer a rotational movement from the electric motor to the impeller, wherein at least one of the at least one flexible cable comprises a plurality of cable elements that are coupled to each other in series to form the flexible cable, wherein the cable elements are coupled to each other such that a rotational movement can be transferred by means of the flexible cable by applying a torque, wherein the cable elements are at least partially configured to decouple from each other if the applied torque exceeds a predetermined maximum torque.

2. The blood pump of claim 1, further comprising a bearing housing distinct from and arranged between the pump housing and the motor housing, the bearing housing comprising at least one axial and/or radial bearing, wherein the at least one flexible sheath comprises a proximal flexible sheath extending proximally from the bearing housing and a distal flexible sheath extending distally from the bearing housing, wherein the at least one flexible cable comprises a proximal flexible cable extending through the proximal flexible sheath so as to receive a rotational movement caused by the electric motor and a distal flexible cable extending through the distal flexible sheath so as to transfer the rotational movement to the impeller.

3. The blood pump of claim 2, further comprising a gear box comprising a gearing mechanism configured to increase or decrease a speed of a rotational movement transferred from the electric motor to the impeller, the gear box being distinct from and arranged between the bearing housing and the motor housing, wherein the at least one flexible sheath further comprises a middle flexible sheath extending between the gear box and the bearing housing, the distal flexible sheath extending distally from the bearing housing, wherein the at least one flexible cable further comprises a middle flexible cable extending through the middle flexible sheath so as to transfer the rotational movement at increased or decreased speed from the gearing mechanism to the bearing.

4. The blood pump of claim 1, wherein the pump housing comprises at least one radial and/or axial bearing configured to center the impeller inside the pump housing.

5. The blood pump of claim 1, wherein the pump housing comprises at least one magnet to form a magnetic coupling between the impeller and the at least one flexible cable.

6. The blood pump of claim 1, wherein the at least one flexible sheath further comprises a further proximal flexible sheath extending proximally from the motor housing, wherein at least one electric wire extends through the further proximal flexible sheath and is connected to the electric motor to supply electric power to the electric motor.

7. The blood pump of claim 1, wherein the cable elements comprise a plurality of snap elements that are fitted together to form a snap drive cable.

8. The blood pump of claim 7, wherein each of the snap elements has a ball and a cup, wherein the ball is configured to snap and rotationally lock inside a cup of another snap element.

9. The blood pump of claim 7, wherein each of the snap elements has a locking tip and a locking groove, wherein the locking tip is configured to mechanically engage a locking groove of another snap element, wherein an extent of force of engagement of the locking tip and locking groove determines the maximum torque the snap drive cable can transmit before the locking tip mechanically disengages from the locking groove to thereby decouple the snap elements from each other.

10. The blood pump of claim 1, wherein the cable elements are coupled to each other via magnetic couplings.

11. The blood pump of claim 10, further comprising an inflow cannula extending distally from the pump housing, being fluidly coupled to the pump housing and providing a blood flow inlet at a distal end portion.

12. The blood pump of claim 11, further comprising an expandable outflow cannula, wherein a distal end of the outflow cannula is attached to the pump housing, the outflow cannula ex-tending proximally from the pump housing so as to be placed across a heart valve separating its distal end from its proximal end to create a one way fluid flow through the percutaneous blood pump.

13. The blood pump of claim 12, wherein the outflow cannula comprises longitudinal reinforcements, preferably made of a shape-memory material, extending from the cannula's proximal end to its distal end, wherein the longitudinal reinforcements attach to an annular ring at the proximal end of the outflow cannula that is placed around the flexible sheath to allow a sliding movement of the annular ring along the flexible sheath.

14. The blood pump of claim 13, further comprising a pump head cage extending distally from the pump housing and configured to keep the pump housing away from surrounding tissue.

15. The blood pump of claim 12, wherein the pump head cage is a pump head sensor cage configured to function as a sensor sensing at least one of the position of the individual parts of the cage and thereby a distance of pump housing from the surrounding tissue, a contraction phase of the ventricle, relative or absolute ventricular volume, a speed of ventricular contraction, an ejection fraction of the ventricle, a location of any localized infracted myocardium, and an electrocardiography (EKG) of the heart.

16. An introducer system, configured for insertion of a percutaneous blood pump of claim 1 into a patient's vessel through an opening in the patient's skin, the system comprising:

an expandable structure, a dilator and an insertion sheath, wherein the insertion sheath has a tubular body that is configured to receive the expandable structure in a compressed form and the dilator inside the expandable structure to form a structure that is configured to be inserted as a unity into the patient's vessel, wherein the expandable structure is configured to be advanced out of the insertion sheath to allow the expandable structure to expand from the compressed form to an expanded form with increased diameter compared to the compressed form.

17. The introducer system of claim 16, further comprising a vessel dilating balloon catheter which is configured to expand the expandable structure by inflating the balloon catheter inside the expandable structure to cause a permanent deformation and expansion of the expandable structure.

18. The introducer system of claim 16, wherein the expandable structure is a tubular metallic structure such as nitinol, or polymeric structure that self-expands to cause a permanent deformation and expansion of expandable structure.

19. The introducer system of claim 18, wherein the vessel dilating balloon catheter comprises a catheter and one or more dilating balloons, the catheter having an inner lumen along its length to allow passage of a guide wire, and at least one of the dilating balloons is in communication with the vessel dilating balloon catheter by means of a separate lumen adjacent to the inner lumen, which allows the passage of fluid to cause balloon inflation or deflation.

20. The introducer system of claim 16, further comprising an inner liner that lines an inner surface of the expandable structure and is a thin polymeric or non-polymeric jacket ranging in thickness from 0.001 mm to 0.5 mm, wherein the inner liner is at least partially attached to the inner surface of the expandable structure or free floating.

21. The introducer system of claim 16, further comprising an outer liner that lines an outer surface of the expandable structure and is configured to abut an inner wall of the patient's vessel, wherein the outer liner is at least partially attached to an outer surface of the expandable structure or free floating.

22. The introducer system of claim 16, further comprising a dilator balloon catheter and an outer balloon, wherein the dilator balloon catheter is mounted on an outer surface of the dilator and is configured to be inflated after the expandable structure is expanded to provide inner support to the expandable structure, wherein the outer balloon is configured to be inflated while the dilator balloon catheter is inflated.

23. The introducer system of claim 16, further comprising a closure device that is configured for closing a puncture site through which the insertion sheath has been inserted into the patient's vessel after removal of the insertion sheath.

24. A kit, comprising:
a pump housing with an impeller housed in the pump housing, the impeller being rotatable so as to cause blood to be drawn into and through the pump housing;
a motor housing an electric motor for causing a rotational movement, the motor housing being distinct from the pump housing and spaced apart from the pump housing in a proximal direction;
at least one flexible sheath extending between the motor housing and the pump housing and at least one flexible cable extending through the flexible sheath so as to transfer a rotational movement from the electric motor to the impeller, wherein the at least one flexible cable comprises cable elements coupled to each other via magnetic couplings in series to form the flexible cable;
an inflow cannula extending distally from the pump housing, being fluidly coupled to the pump housing and providing a blood flow inlet at a distal end portion;
an expandable outflow cannula, wherein a distal end of the outflow cannula is attached to the pump housing, the outflow cannula extending proximally from the pump housing so as to be placed across a heart valve separating its distal end from its proximal end to create a one way fluid flow through the percutaneous blood pump;
an expandable structure;
a dilator; and
an insertion sheath, wherein the insertion sheath has a tubular body that is configured to receive the expandable structure in a compressed form and the dilator inside the expandable structure to form a structure that is configured to be inserted as a unity into the patient's vessel, wherein the expandable structure is configured to be advanced out of the insertion sheath to allow the expandable structure to expand from the compressed form to an expanded form with increased diameter compared to the compressed form.

\* \* \* \* \*